US010184921B2

(12) United States Patent
Neal

(10) Patent No.: US 10,184,921 B2
(45) Date of Patent: Jan. 22, 2019

(54) GAS CHROMATOGRAPH COLUMN CONNECTION DEVICE

(71) Applicant: PerkinElmer Health Sciences, Inc., Waltham, MA (US)

(72) Inventor: Timothy P. Neal, Harwinton, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 530 days.

(21) Appl. No.: 14/821,279

(22) Filed: Aug. 7, 2015

(65) Prior Publication Data

US 2017/0038348 A1  Feb. 9, 2017

(51) Int. Cl.
*G01N 30/60* (2006.01)
*B01D 15/22* (2006.01)

(52) U.S. Cl.
CPC ......... *G01N 30/6026* (2013.01); *B01D 15/22* (2013.01)

(58) Field of Classification Search
CPC .............................. B01D 15/14; G01N 30/60
See application file for complete search history.

(56) References Cited

U.S. PATENT DOCUMENTS

| | | |
|---|---|---|
| 4,991,883 A | 2/1991 | Worden |
| 5,163,215 A | 11/1992 | Ledford, Jr. |
| 5,163,722 A | 11/1992 | Worden |
| 5,215,340 A | 6/1993 | Ledford, Jr. |
| 5,234,235 A | 8/1993 | Worden |
| 5,236,668 A | 8/1993 | Higdon |
| 5,601,785 A | 2/1997 | Higdon |
| 6,102,449 A | 8/2000 | Welsh |
| 6,186,012 B1 | 2/2001 | Kenny et al. |
| 8,062,516 B2 | 11/2011 | Silva et al. |
| 2015/0108749 A1 | 4/2015 | Walsh et al. |

FOREIGN PATENT DOCUMENTS

| | | |
|---|---|---|
| EP | 0841564 A1 | 5/1998 |
| GB | 913142 A | 12/1962 |

OTHER PUBLICATIONS

"Agilent Self Tightening Column Nut and Gas Chromatography Connection Supplies." USA: Agilent Technologies, Mar. 6, 2014.
Lynam, Ken. "Proof of Long-Term, Leak-Free Performance for a Novel Self-tightening GC Column Nut." Agilent Technologies. Nov. 22, 2013: 1-10.

*Primary Examiner* — Kathryn Wright
(74) *Attorney, Agent, or Firm* — Rhodes IP PLC; Christopher R. Rhodes

(57) ABSTRACT

A column connection device for use in gas chromatography is disclosed. The column connection device includes a housing with a piston, a piston spring retainer, and disk springs composed of an austenite nickel-chromium-based superalloy (e.g. Special Metals Corp.'s Inconel family of metals). The piston has a ferrule on its exposed end. The disk springs urge the ferrule against the mating portion of an external device maintaining a seal with the external device and creating a seal radially around a column disposed within. The column connection device also includes a release slider and a column base with a column retainer, column tab, and wire springs composed of an austenite nickel-chromium-based superalloy. The wire springs urge the column tab to frictionally engage the column, thereby inhibiting column movement. Depressing the release slider flexes the wire springs, urging the column tab away from the column, removing the frictional inhibition.

20 Claims, 6 Drawing Sheets

GAS CHROMATOGRAPH COLUMN CONNECTION DEVICE

FIELD

The present application pertains to connection devices in the field of gas chromatography. More specifically, the application pertains to an apparatus for connecting a column to a receiving portion in a gas chromatography instrument.

BACKGROUND

Connection devices are commonly used in many scientific fields, including gas chromatography. These uses are well known in the art, and include passing fluid from one conduit to another. To properly perform their functions, connection devices must provide effective seals to ensure accurate testing results.

The gas chromatography field often involves performing tests using extreme temperatures, both high and low. These temperatures can affect connection devices, and thereby alter test results. For example, extreme temperatures have been known to deform connection device parts by expansion or contraction. Extreme temperatures can also cause reorientation or cracking of the connection device components. In these cases and others, the connection device's seals can be affected, permitting gas or other fluid to leak. Also the ferrule will typically undergo a permanent deformation known as compression set. The ferrule is not cracked or broken, but without a temperature compensating load, a small gap can form between the ferrule and it's mating surface, causing leakage.

In addition, thermocycling—alternating between extreme hot temperatures, extreme cold temperatures, and temperate temperatures—can cause cracking, deformation, or reorientation of connection device components, including loosening of threaded parts, etc. One of skill in the art will appreciate the effects of thermocycling on connection devices and the potential for breaking the device's seals and permitting gas or fluid leak.

Moreover, a particular test may require the column, whether packed or capillary, to be set to a particular depth within the instrument cavity. Furthermore, the column's depth may need to be adjusted accurately, or a column may need to be removed and replaced.

Thus, there remains a need in the art for a column connection device employing a method for easily and accurately adjusting the column depth during installation. It would be additionally beneficial to employ a method permitting adjustments to the depth once the connection device is secured to an external device. It is further desirable to provide a single unit connection device with as few removable components as practicable. These needs are in addition to remaining concerns regarding reliable sealing of the connection device around the column and in relation to an external device.

SUMMARY

Accordingly, it is an object of the present application to provide a column connection device for use in gas chromatography capable of maintaining a fluid-tight seal in the face of extreme temperatures that also provides for easy, consistent, and accurate adjustment to column depth, thereby overcoming the aforementioned disadvantages of the current applications available in the art. It is a further object of the application to provide an easy to use connection device without extraneous parts that could be lost or damaged.

These goals are accomplished, in certain embodiments disclosed herein, by using a series of biasing mechanisms to maintain the required compression load on the column seal regardless of varying temperatures. In some embodiments, the biasing mechanisms are springs or, more specifically, disc springs composed of an austenite nickel-chromium-based superalloy. One example of such a superalloy is Special Metals Corp.'s Inconel family of metals. Those of skill in the art will recognize other potential substitutes. Such embodiments continually urge a ferrule composed of malleable material into the external device's mating portion, ensuring a consistent, effective seal both radially around the column and with the external device. In addition, the biasing mechanisms of such embodiments comprise materials ensuring that deformation and reorientation will not occur despite the extreme temperatures and thermocycling common in a gas chromatograph.

The above-described goals are accomplished, in certain embodiments, by utilizing a column release feature that is easily engaged and disengaged as required during column installation and adjustment. In some embodiments, a biasing mechanism is used to frictionally engage the column and a release slider to disengage the column for adjustment or removal. In some embodiments, the biasing mechanism may be a spring or, more specifically, a wire spring composed of an austenite nickel-chromium-based superalloy (e.g. Special Metals Corp.'s Inconel family of metals). These embodiments are easily operable using a single hand and do not include extraneous parts that might be lost or damaged.

According to one aspect of the technology described herein, a column connection apparatus is comprised of a column base and a release slider. The column base is comprised of a column retainer, a column tab, and a column biasing mechanism. In its resting state, the apparatus's column biasing mechanism urges the column tab toward the column retainer. When the column is inserted therebetween, the column tab and column retainer frictionally engage the column. When the release slider is depressed, the column biasing means urges the column tab away from the column retainer, thereby reducing the frictional engagement of the column within the column base. In some embodiments disclosed herein, frictional engagement of the column is removed entirely, permitting the column to move freely within the column base.

According to another aspect of the technology described herein, the column connection apparatus is comprised of a housing and sealing assembly, the sealing assembly comprising a piston, a piston biasing mechanism at a first end, and a ferrule at a second end. In some embodiments, the sealing assembly further comprises a piston retainer and/or retaining pins. The piston biasing mechanism urges the piston toward its second end, thereby urging the ferrule toward an external device to form a seal with the mating portion of the external device, such as a gas chromatograph's injector or detector.

According to yet another aspect of the technology described herein, the column biasing mechanism comprises one or more spring wires. According to still another aspect of the technology, the piston biasing mechanism comprises one or more disc springs. As can be understood by one of skill in the art, disc springs can effectively maintain sufficient compression load on the piston to ensure the seal remains fluid-tight despite any deformation or reorientation of the connection device components caused by the extreme temperatures.

According to still another aspect of the technology, the piston biasing mechanism and/or the column biasing mechanism are composed of an austenite nickel-chromium-based superalloy. While a person of skill in the art will recognize that variations are possible, Special Metals Corp.'s Inconel X-750 or other members of the Inconel family may be used to maintain spring forces in high temperature environments, for example where temperatures may exceed 450° Celsius.

According to still another aspect of the technology, a portion of the housing's outer surface is threaded. While a person of skill in the art will recognize potential variations, the threading may be M6×1 threading. Such threading helps to ensure a gas tight seal between the piston's ferrule and the mating part of the external device, such as a gas chromatograph's injector or detector.

According to yet another aspect of the technology, the column is disposed along the column connection apparatus's longitudinal axis. One of skill in the art will recognize potential variations whereby the column may be slightly off center or disposed even more substantially to one side of the apparatus.

According to yet another aspect of the technology, the column connection apparatus is comprised of a knob for gripping the apparatus and installing it into an external device, such as a gas chromatograph's injector or detector.

According to still another aspect of the technology, the column base component of the column connection apparatus can rotate independently of the housing and sealing assembly. As one of skill in the art would surely recognize, this aspect of the technology would permit attachment of the apparatus to an external device, such as a gas chromatograph's injector or detector, without twisting the column.

According to yet another aspect of the technology, the release slider moves in a direction perpendicular to the column connection apparatus's longitudinal axis. In some embodiments, the release slider may move at an angle to the longitudinal axis or even along the longitudinal axis, as one of skill in the art will recognize potential variations.

According to still another aspect of the technology described herein, a testing apparatus employing the column connection apparatus is provided. The testing apparatus may be, for example, a gas chromatograph. One or more column connection devices may be employed therein, in connection with, for example, the gas chromatograph's injector and/or detector.

Other objects of the technology described herein and its particular features and advantages will become more apparent from consideration of the following drawings and accompanying detailed description.

DETAILED DESCRIPTION

Figure 1:
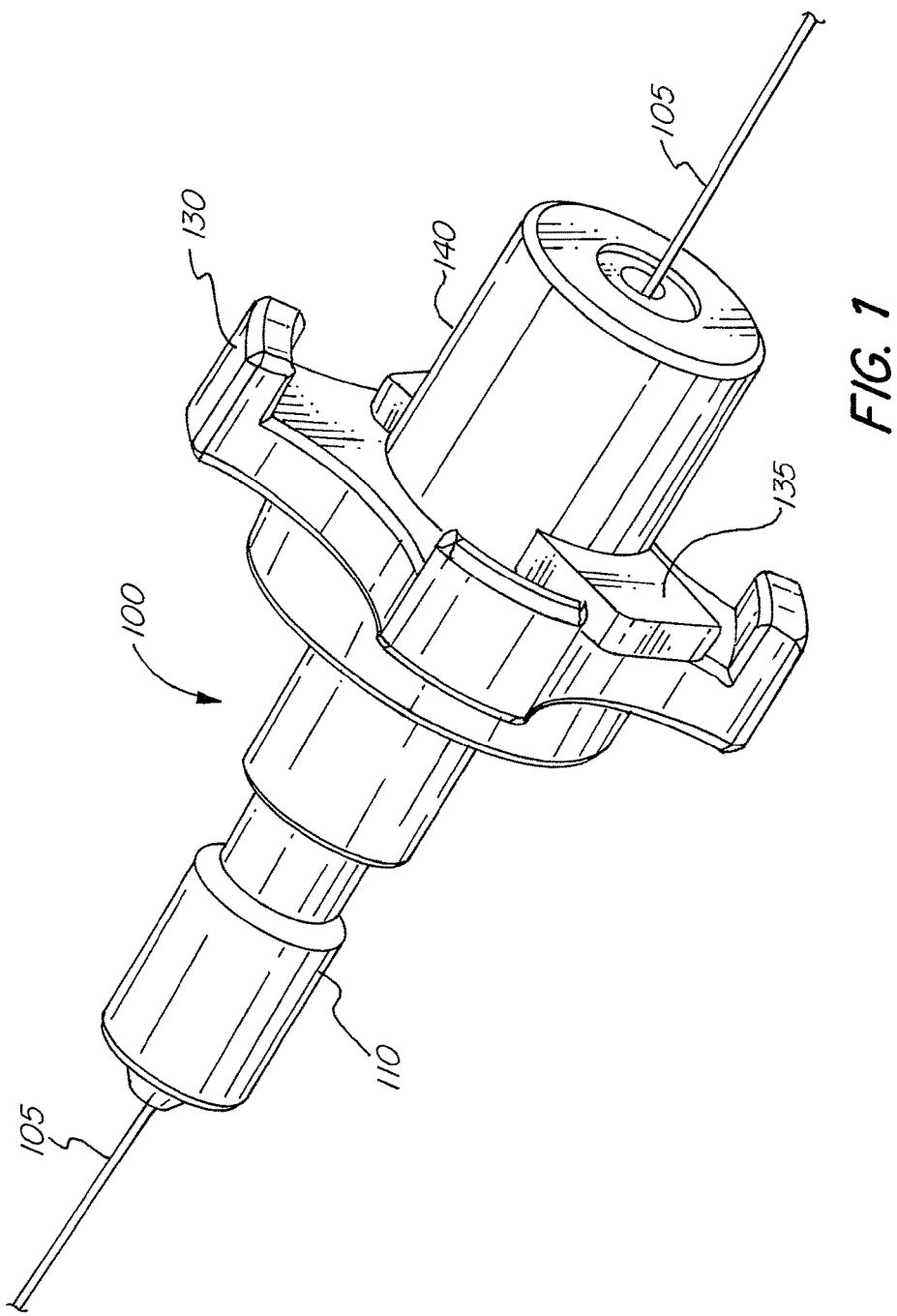
FIG. 1 illustrates an isometric view of a column connection device according to exemplifying embodiments of the technology described herein.

Many attempts have been made in the gas chromatography field to ensure the maintaining of a fluid-tight seal despite the extreme temperatures and/or thermocycling often associated therewith. These attempts include using specific materials, such as malleable materials including graphite or the like, using particular shapes and orientations, such as a frustoconical ferrule and mating portion, using mechanical devices to urge the components together, such as springs and self-compensating nuts, manual tightening of the connection device, and others that are known in the art. Some examples of these efforts are reflected in U.S. Pat. No. 6,102,449 ('449).

Historical approaches used a threaded connection device to manually screw into a receiving device, such as the injector or detector of a gas chromatograph, theoretically creating a seal through the pressure created by the threaded connection. However, as one of skill in the art will surely appreciate, such an approach was unreliable in creating a seal to begin with, and any deformation or reorientation of the connection device during use would likely break the seal and permit fluid leakage.

One historical approach was to use a ferrule composed of a malleable material, such as graphite, and forcing that ferrule into the mating portion of an external device manually through the aforementioned threading approach or otherwise, causing the ferrule to conform in shape with the mating portion creating a first seal, and causing the ferrule to conform radially around a column disposed within and creating a second seal. However, drawbacks of such an approach are well known in the art, and include potential damage to components during insertion and the loss of conforming shape due to extreme temperatures and thermocycling. In each of these cases, the seals may be broken and fluid leakage may occur.

This approach was commonly combined with using a ferrule of a particular shape, such as a frustoconical shape, or including ridges, notches, flanges, or angles on the ferrule. Each of these designs suffers from the same drawbacks as those above. The ferrule may well form a reliable seal upon insertion, but extreme temperatures and thermocycling can cause deformation and reorientation resulting in a defective seal and leakage. Combining this approach with those above has been used to improve the reliability of the connection device's seals, but the limitations and drawbacks in the extreme conditions present in gas chromatography remain.

Perhaps the most effective heretofore known approach to resolving the leakage concerns incorporates a biasing mechanism to continually urge a ferrule composed of malleable material into a mating portion. The continual pressure encourages the ferrule to conform both with the mating portion and radially around a column continually and in spite of deformations or reorientation (e.g. loosening of threaded components) caused by extreme temperatures and thermocycling. Indeed, the '449 patent itself employs a biasing mechanism to continually urge the ferrule against a mating device forming a seal with the mating device and around the column. However, the '449 patent suffers from limitations of its own. For example, the '449 patent makes no provision for facilitating adjustments to column depth during installation and/or replacement of a column.

Thus, there remains a need in the art for a connection device that addresses the above deficiencies known in the art and that is also capable of providing facilitated installation and removal of a column and adjustment of the depth of a column disposed within. For example, columns are often connected to the injector and/or detector of a gas chromatograph using a column connection device.

A particular test may require the column, whether packed or capillary, to be set to a particular depth within the instrument cavity. Moreover, the column's depth may need to be adjusted accurately, or a column may need to be removed and replaced. Current methods for adjusting or replacing a column are difficult and time consuming and can be inaccurate and/or inconsistent. Examples of methods in the art for adjusting or replacing the column in a connection device are reflected in U.S. Pat. No. 5,215,340 ('340).

Historically, to adjust a column's depth, the connection device would have to be manually disengaged, typically by unscrewing a column nut, from the gas chromatograph, the column adjusted within the connection device either by eye or using a ruler, and the connection device reconnected to the gas chromatograph. This approach suffered from serious drawbacks. It was time consuming and inaccurate. In addition, the column often shifted during reengagement because it was manually held in place, thus affecting its depth.

Similarly, when a column needed to be replaced, the connection device had to be disengaged and the column then removed, replaced, and the connection device reengaged. The depth of the replacement column was set either by eye or using a ruler and, again, often shifted during reassembly.

Early approaches to solving the column depth accuracy issue involved first inserting the column through an inlet septum followed by a column nut and then a ferrule. The column was then cut to the appropriate length above the ferrule and the connection device and column installed into the receiving port of the external device—for example, the injector or detector of a gas chromatograph. The septum was used to inhibit the column depth from changing during installation.

Limitations of this approach included unreliability and inaccuracy of the column's depth as well as the effective sealing concerns discussed above. Furthermore, septa are separate parts subject to misplacement and damage and they may be clumsy to use. Moreover septa may be inadvertently left in place after assembly, thereby causing problems during testing.

To resolve the sealing concerns described above, some methods employed self-tightening column nuts. However, even with the use of self-tightening nuts, the column depth was set using a septum and by manually cutting the column at the desired length by eye or using a ruler. Thus, the same reliability and accuracy concerns remained with respect to column depth. In addition, each of the septum, column nut, ferrule, etc. is separate and must be individually inserted over the column. The several parts make misplacement and damage more likely.

In order to more accurately ensure proper depth of the column, some methods employed a column installation tool, sometimes in addition to a septum. Examples of column installation tools include Agilent Technologies' "Ferrule pre-swaging and MS interface installation tools." Those of skill in the art will appreciate that other column installation tools are available as well. The column installation tool was used to gauge depth of the column and then to pre-swage the ferrule onto the column to improve consistency of the column depth. However, the ferrule was still subject to sliding along the column even after pre-swaging. Thus, some approaches combined the column installation tool with a septum to provide further assurance of accurate column depth.

Limitations to this approach remained, however, including slippage during installation and the inability to easily adjust the column depth without removing the entire connection device. Similarly, the connection device needed to be disassembled to replace a column. Moreover, column installation tools, like septa, are separate parts subject to misplacement and damage and are clumsy to use, requiring skill on the part of the operator.

The following description illustrates the technology that is the subject of the preset application by way of example, not by way of limitation of the principles thereof. This description will enable one skilled in the art to make and use the technology and describes several embodiments, adaptations, variations, alternatives, and uses of the technology, including what is presently believed to be the best mode of carrying out the technology. However, this technology may be embodied in several forms and should not be construed as limited to the embodiments set forth herein; rather, these embodiments are provided by way of example so that this disclosure will convey the scope of the technology to those skilled in the art.

Referring first to FIG. 1 depicting an exemplary embodiment of the technology, a column connection device 100 is shown comprising an upper housing 110, a knob 130 for facilitating installing or removing the connection device, a release slider 135, and a lower base 140. As can be seen, a column 105 is disposed through the column connection device 100.

Figure 2:
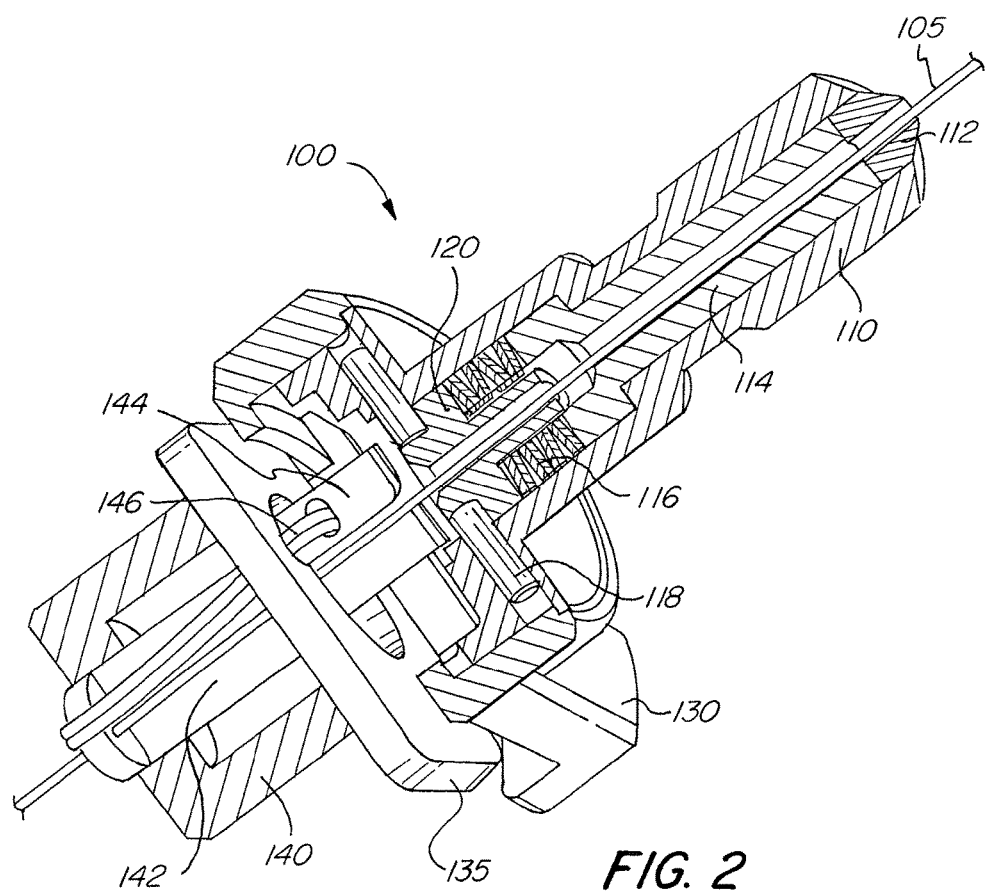
FIG. 2 illustrates an isometric, partially cross-sectional view of a column connection device according to the exemplary embodiment of the present technology depicted in FIG. 1.

Referring next to FIG. 2 showing a partially cross-sectional view of FIG. 1's exemplary embodiment of the technology, the upper housing 110 contains a ferrule 112, a piston 114, and a biasing mechanism 116, such as a spring or set of springs. A column 105 can be disposed through the upper housing 110, as illustrated. In some embodiments, the ferrule 112 is composed of graphite or other malleable materials known to those of skill in the art to facilitate sealing around the column 105. Likewise, the ferrule 112 may have a frustoconical shape and/or include ridges, notches, flanges, or angles in some embodiments. The advantages of such designs will be apparent to those of skill in the art.

In some embodiments, the biasing mechanism 116 is fashioned to urge the piston 114 toward the ferrule 112 to pressure the ferrule against an external device, thereby forming two seals: one between the ferrule 112 and the external device and one between the ferrule 112 and the column 105. As will be appreciated by one of skill in the art, the biasing mechanism 116 acts on the piston 114 to continually urge the ferrule 112 toward the external device, thereby facilitating continual sealing even in the face of extreme temperatures and thermocycling, which may cause deformation or reorientation of the ferrule 112 or other components during use. In some embodiments, the biasing mechanism 116 is positioned directly behind the ferrule 112 and directly urges the ferrule against an external device, accomplishing the same objectives as discussed above.

Placing the biasing mechanism 116 at a distance from the ferrule 112 may have the added advantage of insulating the biasing mechanism 116 from the extreme external environment.

In some embodiments, the biasing mechanism 116 comprises a spring or set of springs. The spring or set of springs may comprise one or more disk springs, in some embodiments. As can be appreciated by one of skill in the art, the use of disk springs helps to ensure continual biasing of the ferrule 112 toward the external device and, thereby, continual sealing of the ferrule 112 with the external device and around the column 105. In some embodiments, the biasing mechanism 116 comprises an austenite nickel-chromium-based superalloy (e.g. Special Metals Corp.'s Inconel family of metals). One of skill in the art will recognize the advantage of the use of an austenite nickel-chromium-based superalloy, which is resistant to deformation when exposed to high temperature environments.

In some embodiments, the upper housing 110 further comprises a spring retainer 120. The spring retainer 120 can act as an immobile backstop for the biasing mechanism 116 such that the force generated by the biasing mechanism 116 continues to urge the ferrule 112 toward the external device. In some embodiments, the upper housing 110 also contains one or more retaining pins 118. The retaining pins 118 likewise act to immobilize the spring retainer 120 and ensure the force generated by the biasing mechanism 116 continues to urge the ferrule 112 toward the external device.

In some embodiments, the upper housing 110 has a threaded outer surface. The threaded surface is used to engage with the threaded surface of an external device. One of skill in the art will recognize the advantages of this design, which include facilitating installation of the connection device 100 and urging the ferrule 112 toward the external device, thereby creating a seal. In some embodiments, the threading employed may be M6×1 threading.

Also apparent in FIG. 2's partially cross-sectional view of the column connection device is the composition of the lower base unit 140. As illustrated, the column 105 can be disposed through the lower base unit 140 and can extend a chosen distance out the bottom of the connection device 110. To facilitate the adjustment of the column 105, the base 140 comprises a column retainer 142, a column tab 144, and a second biasing mechanism 146. The biasing mechanism 146 is fashioned to urge the column tab 144 toward the column retainer 142, frictionally engaging the column 105 therebetween. The frictional engagement of the column tab 144 and column retainer 142 with the column 105 stabilizes the column's depth during installation of the connection device 100.

To adjust the column depth, the user can depress the release slider 135, removing the frictional engagement with the column 105 and permitting it to be freely adjusted within the column base unit 140. Specifically, depressing the release slider 135 urges the biasing mechanism 146, which in turn urges the column tab 144 away from the column retainer 142, thus removing the frictional engagement with the column 105. Once the user has adjusted the column 105 to the desired depth, the release slider 135 is released and the biasing mechanism 146 urges the column tab 144 toward the column retainer 142 once again, frictionally engaging the column 105 to prevent any change to the depth during installation.

In some embodiments, the biasing mechanism 146 comprises a spring or set of springs. The spring or set of springs may comprise one or more wire springs, in some embodiments. As can be appreciated by one of skill in the art, the use of wire springs helps to ensure continual biasing of the column tab 144 toward the column retainer 142 and, thereby, frictional engagement of the column 105 between the column tab 144 and the column retainer 146. In some embodiments, the biasing mechanism 146 comprises an austenite nickel-chromium-based superalloy (e.g. Special Metals Corp.'s Inconel family of metals). One of skill in the art will recognize the advantage of the use of an austenite nickel-chromium-based superalloy, which is resistant to deformation when exposed to high temperature environments.

Figure 3:
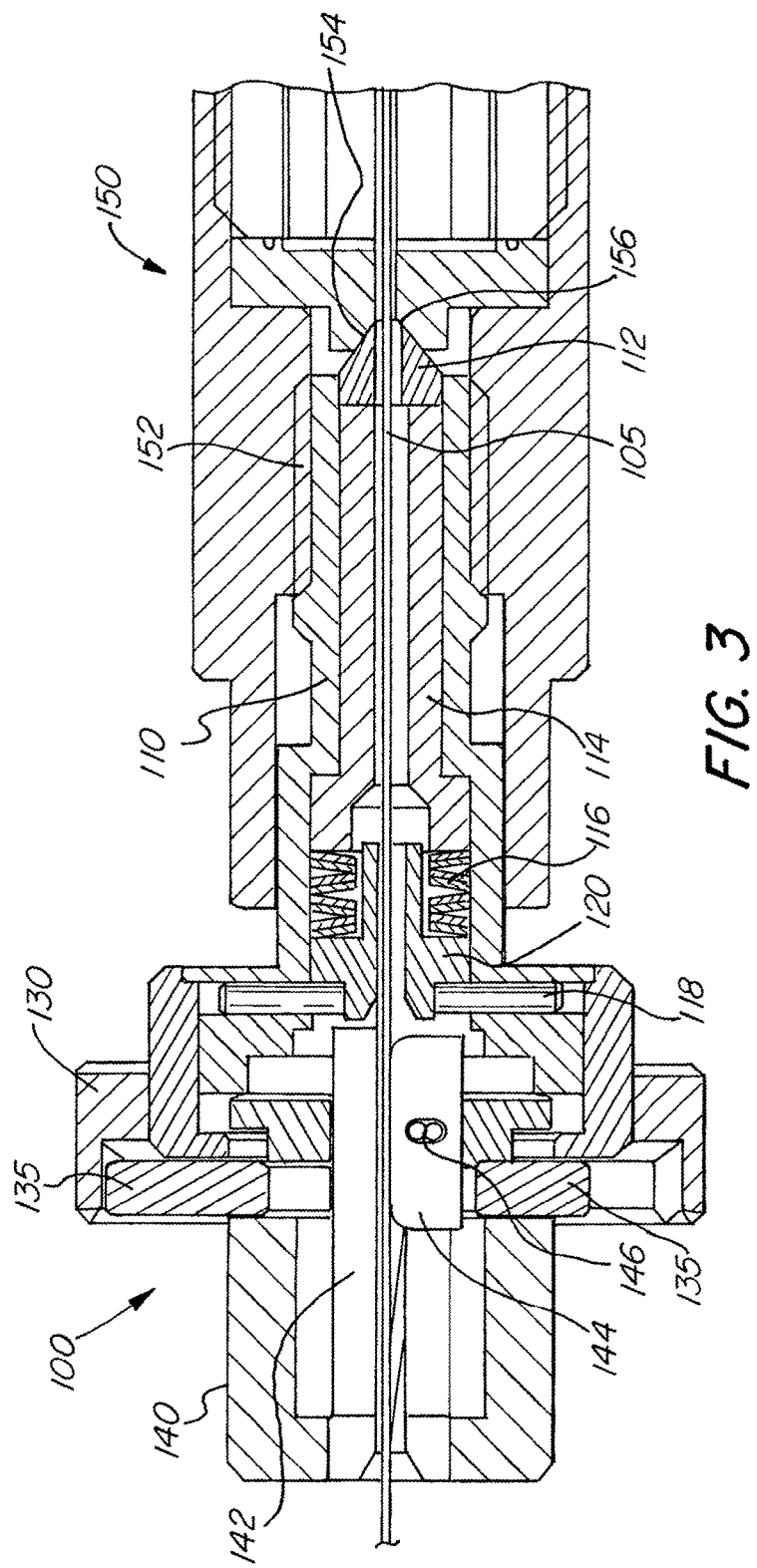
FIG. 3 illustrates a partially cross-sectional view of a column connection device installed in the mating portion of an external device, such as the injector or detector of a gas chromatograph, in accordance the exemplary embodiment of the present technology depicted in FIGS. 1 and 2.

Referring now to FIG. 3, a column connection device 100 is shown in connection with an external device 150, such as an injector or detector of a gas chromatograph. In some embodiments, the outer surface of upper housing 110 is threaded such that the threaded housing surface intertwines with a threaded surface of the external device 150 at an area such as that depicted at 152. As will be appreciated by one of skill in the art, the intertwining of the housing's 110 outer surface with an adjacent surface of the external device 150 facilitates installation of the connection device 100.

Further, tightening the connection device 100 into the external device 150 facilitates a seal between ferrule 112 and a surface of the external device. The seal 154 ensures that fluid does not escape from any gap between the ferrule 112 and the external device 150. In addition, in some embodiments the ferrule 112 may have a particular shape, such as a frustoconical shape. In these instances, the pressure applied to the ferrule 112 when the connection device 100 is tightened into the external device 150 creates a second seal with the ferrule 112 compressing radially around the column 105 at the ferrule's tip 156. In some embodiments, the connection device 100 is tightened through the use of the knob 130 or other, comparable component. Those of skill in the art will recognize the various options available to accomplish this objective.

In some embodiments, the column connection device 100 is constructed to permit the knob 130 (or other, comparable component) and upper housing 110 to rotate independent from the column 105 and column base 140. Thereby, the connection device 100 can be tightened into an external device without simultaneous rotation of the column 105 and column base 140. This functionality may be important to avoid excessive twisting pressure on the column 105, which could cause damage and/or affect the column's functionality.

In addition to the sealing pressure facilitated by tightening the connection device 100 into the external device 150, in some embodiments the biasing mechanism 116 urges the piston 114 against the ferrule 112 to generate additional, continuous pressure between the ferrule 112 and the external device 150. In some embodiments, the biasing mechanism 116 directly abuts the ferrule 112, urging it toward the external device 150. As those of skill in the art will appreciate, the pressure generated by the biasing mechanism 116 helps to ensure the seal 154 is maintained throughout use, especially when the connection device 100 is used in experiments using a gas chromatograph, wherein parts are prone to deformation and reorientation due to extreme temperatures and thermocycling. Similarly, the pressure generated by the biasing mechanism 116 on the ferrule 112 helps to ensure a seal is maintained radially around the column at the ferrule tip 156 despite any deformation or reorientation caused by the environment during use.

Also depicted in FIG. 3 is the column base 140 and column retainer 142, column tab 144, and biasing mechanism 146 according to certain embodiments of the present technology. As can be seen in FIG. 3, the connection device 100 is in its natural, resting state, in which the biasing mechanism 146 urges the column tab 144 toward the column retainer 142, frictionally engaging the column 105 therebetween.

In some embodiments, to adjust the depth of the column within the connection device, a user need simply depress the release slider 135 perpendicular to the connection device's longitudinal axis, thereby urging the column tab 144 away from the column retainer 142 and releasing the frictional engagement on the column 105. In some embodiments the release slider 135 may be depressible at other angles and directions. Once the column 105 has been adjusted to the desired depth, the user simply releases the release slider 135 and the column base will return to its natural state, frictionally engaging the column 105 to ensure the chosen column depth is maintained during installation.

Figure 4:
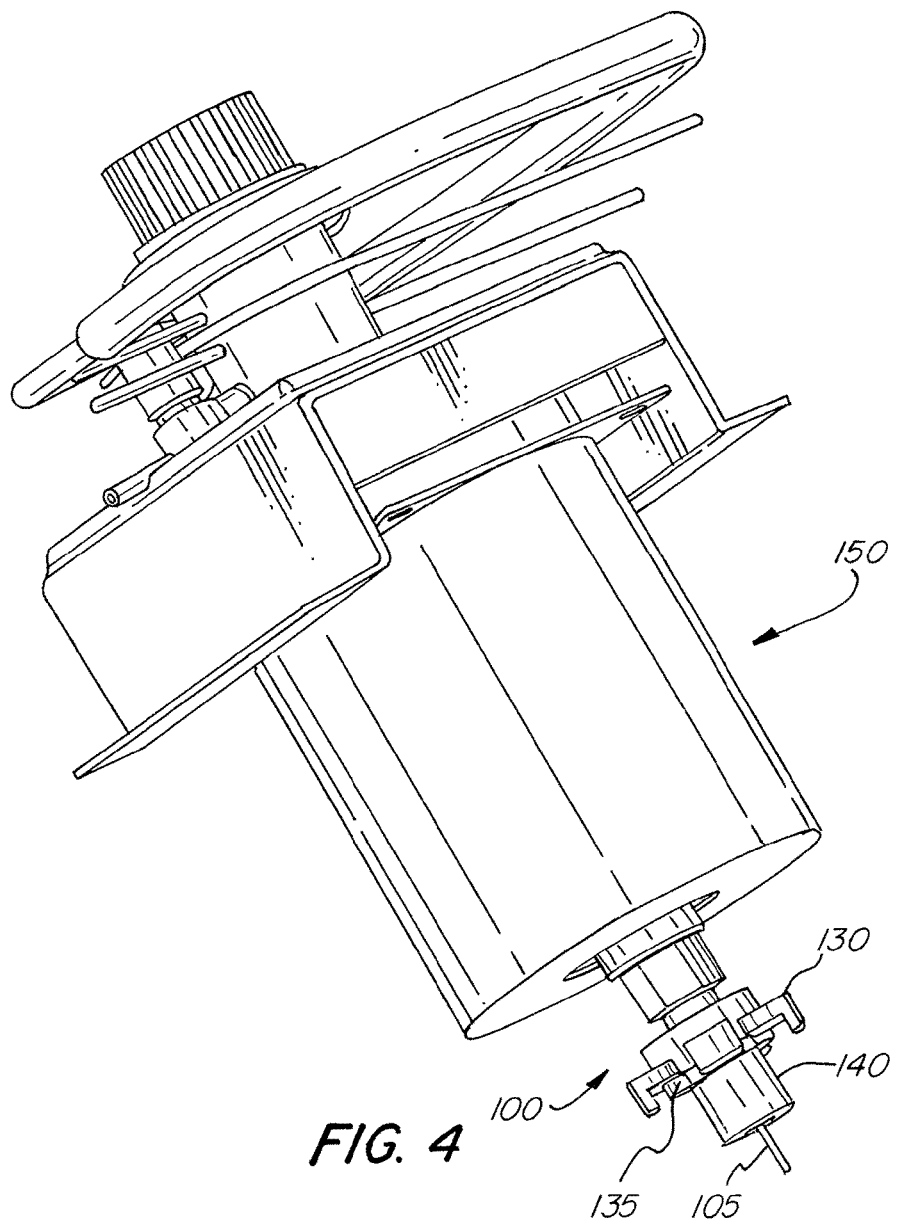
FIG. 4 illustrates a broader view of a column connection device installed in the mating portion of an external device, such as the injector or detector of a gas chromatograph, in accordance with the exemplary embodiment of the present technology depicted in FIGS. 1-3.

Referring next to FIG. 4, a column connection device 100 according to FIG. 1's exemplary embodiment of the present technology is shown in use with an external device 150, such as an injector or detector of a gas chromatograph. As depicted, the column connection device 100 has been installed by tightening using the knob 130. Those of skill in the art will recognize the availability of alternative embodiments to accomplish the same objective.

Once the connection device 100 is installed in the external device 150, adjustment to the column's depth may be made by depressing the release slider 135, thereby releasing the frictional engagement of the column tab 144 and column retainer 142 with the column. Once the desired depth has been achieved, releasing the release slider 135 will ensure the column depth is maintained during further installation.

Figure 5:
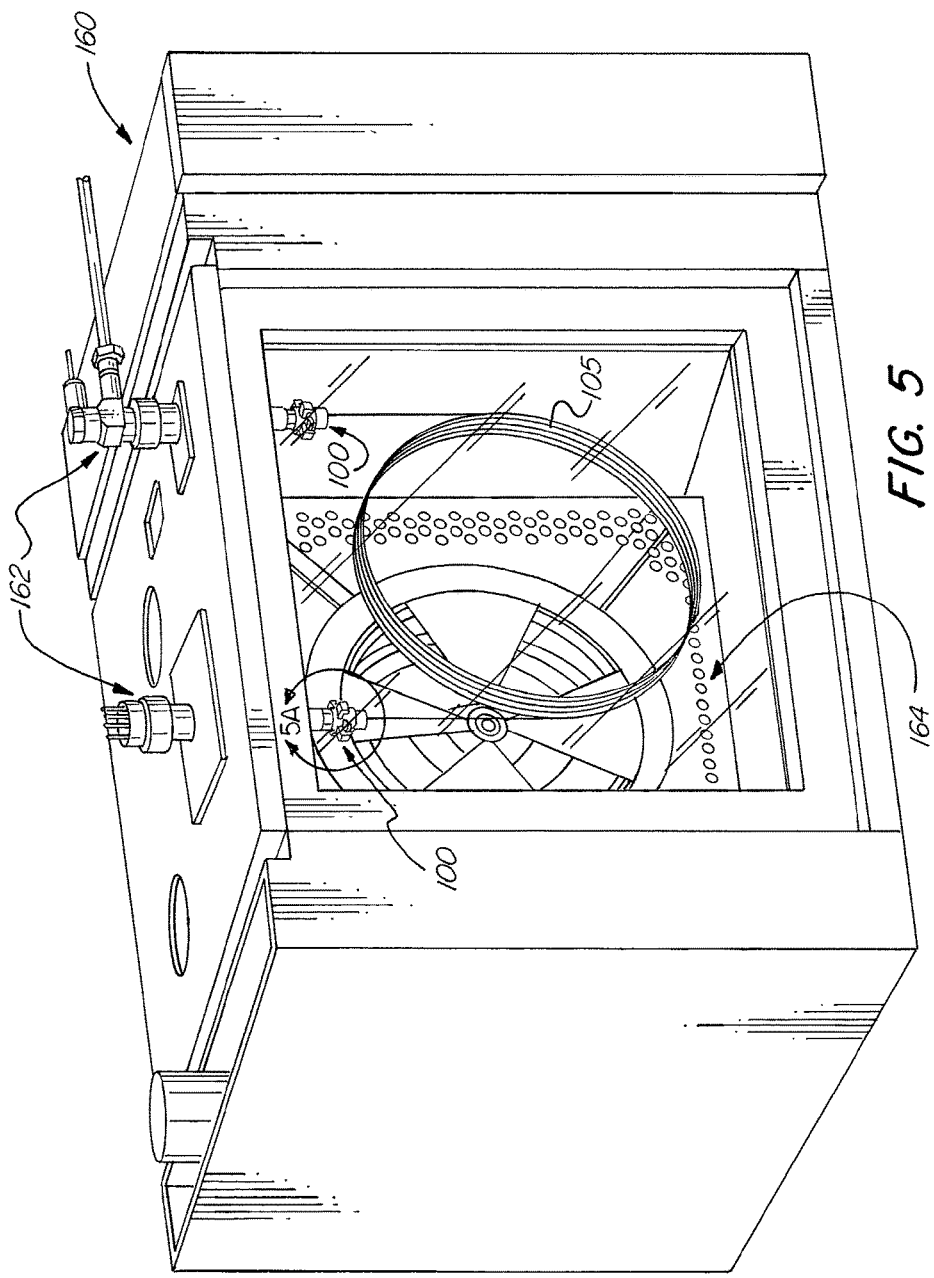
FIG. 5 illustrates an overview of a gas chromatograph with two column connection devices installed in accordance with the exemplary embodiment of the present technology depicted in FIGS. 1-4.

Referring next to FIG. 5, a gas chromatograph 160 is depicted using two column connection devices 100 according to FIG. 1's exemplary embodiment of the present technology. The connection devices 100 are installed in the gas chromatograph's injector/detector 162. The column 105 is hanging within the gas chromatograph's cavity 164. In some embodiments, adjustment to the column's depth is facilitated by depressing the release slider 135, thereby removing the connection device's frictional engagement with the column 105. Once the desired depth is reached, the release slider is released, and the connection device's frictional engagement with the column 105 is resumed, thereby ensuring the selected column depth is maintained during continued installation.

In some embodiments, a user will insert a column 105 within the column connection device 100. When initially inserting the column 105 into the connection device 100, the user will depress the release slider 135 to ensure the column can move within the column base 140 free from frictional engagement by the column tab 144 and column retainer 142. Upon reaching the desired depth of the column 105, the user then releases the release slider 135, whereby the biasing mechanism 146 urges the column tab 144 toward the column retainer 142, frictionally engaging the column 105 therebetween. Accordingly, the depth of the column can be maintained during installation of the column connection device 100 into an external device.

The user next installs the connection device into an external device, such as an injector or detector of a gas chromatograph, by tightening the threaded outer surface of the upper housing 110 into an adjacent threaded surface of the external device. In some embodiments, tightening is accomplished using a knob 130 or other, comparable component. As the connection device 100 is installed, the column depth is maintained through the frictional engagement of the column 105 with the column tab 144 and the column retainer 142 created by biasing mechanism 146.

Once the connection device 100 is secured within the external device, the user can make any adjustments to the column depth quickly and easily by depressing the release slider 135, thereby releasing any frictional engagement between the column 105 and the column tab 144 and column retainer 142. In some embodiments, the connection device 100 will have a scale and/or reference feature to further facilitate accurate column depth. Once the desired depth is reached, the user simply releases the release slider 135 to re-engage the frictional engagement within the column base 140 and ensure no further changes in the column's depth.

The user can then fully tighten the connection device 100 into the external device using the knob 130 or other mechanism. Upon fully tightening the connection device, the ferrule 112 creates a seal 154 with the external device. Likewise, the ferrule 112 seals radially around the column 105 at the ferrule's tip 156, creating a second seal. With both seals in place, fluid leakage during experimentation is avoided.

In some embodiments, in addition to the pressure created by tightening the connection device 100 into the external device, the biasing mechanism 116 continually urges the piston 114 toward the ferrule 112, creating continual pressure between the ferrule 112 and the external device. In some embodiments, the biasing mechanism 116 directly abuts the ferrule 112 to generate continual pressure. The continual pressure ensures both the seal between the ferrule and external device and the seal radially around the column are maintained throughout an experiment, including an experiment in a gas chromatograph involving extreme temperatures and/or thermocycling.

In some embodiments, the column connection device 100 is constructed to permit the knob 130 (or other, comparable component) and upper housing 110 to rotate independent from the column 105 and column base 140. Thereby, the connection device 100 can be tightened into an external device without simultaneous rotation of the column 105 and column base 140. This functionality may be important to avoid excessive twisting pressure on the column 105, which could cause damage and/or affect the column's functionality.

In some applications of the present technology, the user may want to continually adjust the column depth during installation of the connection device 100 within an external device. In such instances, the user can continually depress and release the release slider 135 as necessary during installation. Accordingly, embodiments of the connection device of the present technology accomplish the goal of facilitating quick and accurate adjustments to column depth throughout the installation process. Simultaneously, the design of the upper housing 110, ferrule 112, and biasing mechanism 116 ensure that a fluid tight seal is maintained both between the ferrule 112 and external device and radially around the column 105 during even the most extreme conditions of experimentation within, for example, a gas chromatograph.

Figure 5A:
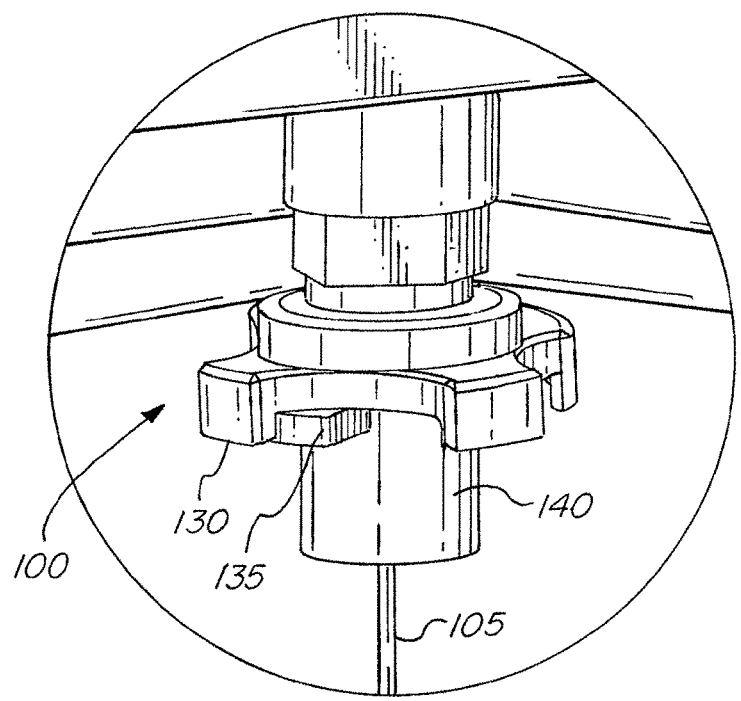
FIG. 5A illustrates a magnified view of one of the column connection devices installed in the gas chromatograph depicted in FIG. 5 in accordance with the exemplary embodiment of the present technology depicted in FIGS. 1-5.

Referring next to FIG. 5A, a magnified view of one of the two column connection devices 100 attached to the gas chromatograph 160 is depicted according to FIG. 5's exemplary embodiment of the present technology. The connection device 100 is installed in the gas chromatograph's injector or detector 162, with the column 105 protruding below the column connection device 100 into the gas chromatograph's cavity 164. In some embodiments, adjustment to the column's depth is facilitated by depressing the release slider 135, thereby removing or reducing the connection device's frictional engagement with the column 105 within the column base 140. Once the desired depth is reached, the release slider 135 is released, and the connection device's frictional engagement with the column 105 is resumed, thereby ensuring the selected column depth is maintained during continued installation.

In some embodiments, the connection device 100 is tightened by gripping and rotating the knob 130 or other, comparable component. In some embodiments, the column connection device 100 is constructed to permit the knob 130 (or other, comparable component) to rotate independent from the column 105 and column base 140. Thereby, the connection device 100 can be tightened into an external device without simultaneous rotation of the column 105 and column base 140. This functionality may be important to avoid excessive twisting pressure on the column 105, which could cause damage and/or affect the column's functionality.

Although the technology has been described with reference to particular embodiments and arrangements of parts, features and the like, these are not intended to exhaust all possible embodiments, arrangements, or features, and indeed many other modifications and variations will be ascertainable to those of skill in the art.

What is claimed is:

1. A column connection apparatus comprising:
    a column base within which a column is movably disposed, the column base comprising a column retainer, a column tab, and a column biasing mechanism;
    a depressible release slider positioned with respect to the column base and in communication with the column tab;
    wherein the column retainer and the column tab define a space therebetween in which the column is slideably disposed, and wherein the column biasing mechanism urges the column tab toward the column retainer to frictionally engage the column between the column tab and the column retainer, thereby inhibiting movement of the column within the column base;
    wherein depressing the release slider reduces the column tab's frictional engagement with the column, thereby reducing inhibition of movement of the column within the column base;
    a housing and sealing assembly surrounding the column, the sealing assembly comprising a piston, a piston biasing mechanism, a piston retainer at the piston's first end, and a ferrule at the piston's second end; and
    wherein the piston retainer and piston biasing mechanism urge the piston toward its second end such that, when abutting a mating portion of an external device, the ferrule forms a first seal around the column.

2. The column connection apparatus of claim 1, wherein the column biasing mechanism urges the column tab to abut the column and press the column against the column retainer.

3. The column connection apparatus of claim 1, wherein depressing the release slider causes the column biasing mechanism to separate the column tab from the column, thereby removing inhibition of movement of the column within the column base.

4. The column connection apparatus of claim 1, wherein the column biasing mechanism comprises at least one spring wire.

5. The column connection apparatus of claim 4, wherein the at least one spring wire comprises an austenite nickel-chromium-based superalloy.

6. The column connection apparatus of claim 1, wherein the piston biasing mechanism comprises at least one disc spring.

7. The column connection apparatus of claim 6, wherein the at least one disc spring comprises an austenite nickel-chromium-based superalloy.

8. The column connection apparatus of claim 1, wherein the ferrule forms a second seal with the mating portion of the external device.

9. The column connection apparatus of claim 1, wherein the column is disposed along the apparatus' longitudinal axis.

10. The column connection apparatus of claim 1, wherein the housing and sealing assembly are rotatable independently from the column, column base, and release slider during assembly.

11. The column connection apparatus of claim 1, wherein the release slider moves in a direction perpendicular to the length of the column when depressed.

12. A testing apparatus comprising the column connection apparatus of claim 1.

13. The testing apparatus of claim 12, wherein the testing apparatus comprises a gas chromatograph.

14. A column connection apparatus comprising:
    a column movably disposed along a longitudinal axis within a housing, the housing comprising an outer surface and an inner surface wherein at least part of said outer surface is threaded;
    a sealing assembly comprising a piston, at least one disc spring comprising an austenite nickel-chromium-based superalloy, a disc spring retainer at the piston's first end, and a ferrule at the piston's second end;
    a column base comprising a column retainer, a column tab, and at least one spring wire comprising an austenite nickel-chromium-based superalloy, wherein the column retainer and the column tab define a space therebetween in which the column is slideably disposed; and
    a release slider depressible in a direction perpendicular to the longitudinal axis;
    wherein the disc spring retainer and the at least one disc spring are positioned to urge the piston toward its second end such that, when abutting a mating portion of an external device, the ferrule forms a first seal around the column;
    wherein the at least one spring wire urges the column tab toward the column retainer to frictionally engage the column between the column tab and the column retainer, thereby inhibiting movement of the column along the longitudinal axis within a housing; and
    wherein depressing the release slider reduces the column tab's frictional engagement with the column, thereby reducing inhibition of movement of the column along the longitudinal axis within a housing.

15. The column connection apparatus of claim 14, wherein the at least one spring wire urges the column tab to abut the column and press the column against the column retainer.

16. The column connection apparatus of claim 14, wherein depressing the release slider causes the at least one spring wire to separate the column tab from the column, thereby removing inhibition of movement of the column along the longitudinal axis within a housing.

17. The column connection apparatus of claim 14, wherein the ferrule forms a second seal with the mating portion of the external device.

18. The column connection apparatus of claim 14, wherein the housing and sealing assembly are rotatable independently from the column, column base, and release slider during assembly.

19. A testing apparatus comprising the column connection apparatus of claim 14.

20. The testing apparatus of claim 19, wherein the testing apparatus comprises a gas chromatograph.

* * * * *